United States Patent [19]

Sato et al.

[11] Patent Number: 4,709,112
[45] Date of Patent: Nov. 24, 1987

[54] PROCESS FOR DIMERIZING LOWER α-OLEFINS

[75] Inventors: Hiroshi Sato, Ibaraki; Kiyoshi Ikimi, Otokuni; Hideto Tojima, Kyoto; Mikoto Takahashi, Oita, all of Japan

[73] Assignee: Sumitomo Chemical Company, Limited, Osaka, Japan

[21] Appl. No.: 947,873

[22] Filed: Dec. 30, 1986

[30] Foreign Application Priority Data

Jan. 6, 1986 [JP] Japan .................................. 61-001168
Mar. 22, 1986 [JP] Japan .................................. 61-064531

[51] Int. Cl.$^4$ ............................................. C07C 2/24
[52] U.S. Cl. .................................... 585/513; 585/527
[58] Field of Search .................................. 585/513, 527

[56] References Cited

U.S. PATENT DOCUMENTS 4,020,118 4/1977 Morikawa et al. .................. 585/513
4,155,946 5/1979 Sato et al. .......................... 585/513

*Primary Examiner*—Curtis R. Davis
*Attorney, Agent, or Firm*—Birch, Stewart, Kolasch & Birch

[57] ABSTRACT

An improved process for dimerizing lower α-olefins using a novel nickel-containing Ziegler catalyst system including
(A) an organic acid salt or complex of nickel,
(B) a trialkylaluminum,
(C) a trivalent phosphorus compound of the formula:

$$PR^1R^2R^3 \quad (I)$$

$$P(NR^1{}_2)_3 \quad (II)$$

$$P(OR^1)_3 \quad (III)$$

wherein $R^1$, $R^2$, $R^3$ are alkyl, cycloalkyl, aryl or aralkyl,
(D) a fluorinated isopropanol of the formula:

$$CF_mH_{3-m}-\underset{\underset{OH}{|}}{CH}-CF_nH_{3-n} \quad (IV)$$

wherein m and n are in $4 \leq m+n \leq 6$, and optionally
(E) a catalyst co-activator: halogenated compounds of the formulae:

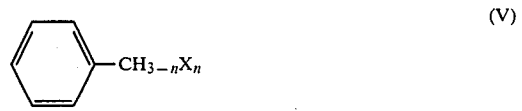

and $$R^4R^5R^6CX \quad (VI)$$

wherein X is halogen, $R^4$, $R^5$, $R^6$ are alkyl, and n is 1 to 3, and further optionally,
(F) a compound selected from aliphatic alcohol and aliphatic carboxylic acid or ester thereof, which yields the dimers with high selectivity of isomers and uniformity of the catalyst without corrosion of the apparatus.

5 Claims, No Drawings

PROCESS FOR DIMERIZING LOWER α-OLEFINS

This invention relates to a process for dimerizing lower α-olefins, and more particularly to an improved process for dimerizing lower α-olefins by using a novel nickel-containing Ziegler type catalyst.

BACKGROUND OF THE INVENTION

Lower α-olefin dimers, such as dimers of ethylene propylene, butene, etc., are usually used as a key material for the preparation of agricultural chemicals, perfumes, formed products, etc. and also as a starting material for producing high molecular weight compounds. It is known that the dimers can be produced by dimerization of monomer(s) by using the following nickel-containing Ziegler type catalyst:

(i) a catalyst comprising a π-allyl nickel complex/an organic aluminum halide compound/an organic phosphine (cf. Japanese Patent Second Publication (Kokoku) No. 34007/1971), (ii) a catalyst comprising a nickel salt/an organic aluminum halide compound/ an organic phosphine (cf. Japanese Patent Second Publication (Kokoku) No. 22807/1972), and (iii) a catalyst comprising a nickel salt/a trialkylaluminum/an organic phosphine/a halogenated phenol/water (cf. Japanese Patent First Publication (Kokai) No. 167932/1982).

However, in the above process (i), there is used as a nickel component a π-allyl nickel complex which is unstable to air, and hence, it is very difficult to handle and further, the complex must be prepared separately by a process having complicated steps.

Moreover, in either process (i) or (ii), an organic aluminum halide compound must be used as the aluminum component, and hence, the halogen atom bound to aluminum atom is easily removed therefrom in the form of HCl etc. due to moisture etc. contained in the system, which unfavorably induces corrosion of apparatus. When a lower olefin such as propylene is used, the fraction of 2,3-dimethylbutenes (hereinafter referred to as "DMBS") in the produced dimer is unfavorably low.

The process (iii) had been accomplished by the present inventors to overcome the above problems associated with the known processes. However, even by this process, there is unfavorably induced lowering of heat-removal capacity of the heat exchanger for cooling during the continuous operation for a long period of time. On analysis of this unfavorable phenomenon, it has been found that it is induced by deposition of fine precipitates on the surface of the heat exchanger which originate from the catalyst, and that the catalyst used in the process (iii) is not necessarily satisfactory in view of non-uniformity of the catalyst.

Thus, the known processes have various problems and are not satisfactory for the industrial production of dimers of α-olefins.

SUMMARY OF THE INVENTION

In order to overcome the above-mentioned problems, the present inventors have studied catalysts systems suitable for the dimerization of lower α-olefins and have found that when a specific fluorinated isopropanol is used instead of the halogenated phenol and water in the catalyst system used in the above process (iii), the reaction system has improved uniformity and can solve the problems in the known processes. Further, the catalytic effeciency and selectivity of the isomers are also improved.

An object of the present invention is to provide an improved proces for dimerizing lower α-olefins by using a novel Ziegler type catalyst including a specific fluorinated isopropanol as the catalyst component.

Another object of the invention is to provide a process for the industrial production of dimers with high selectivity of isomers and high catalytic efficiency without problems such as corrosion of the apparatus, etc. in the known processes.

A further object of the invention is to provide a novel catalyst system suitable for dimerization of lower α-olefins.

These and other objects and advantages of the present invention will become apparent to those skilled in the art from the following description.

DETAILED DESCRIPTION OF THE INVENTION

The process of dimerizing lower α-olefins of this invention is characterized by the use of a catalyst system comprising the following four components (A), (B), (C) and (D) or five components (A), (B), (C), (D) and (E), and optionally (F):

(A) an organic acid salt or complex of nickel,
(B) a trialkylaluminum,
(C) at least one trivalent phosphorus compound of the following formula (I), (II) or (III):

$$PR^1R^2R^3 \quad (I)$$

$$P(NR^1{}_2)_3 \quad (II)$$

$$P(OR^1)_3 \quad (III)$$

wherein $R^1$, $R^2$ and $R^3$ are independently an alkyl, a cycloalkyl, an aryl, or an aralkyl, and (D) a fluorinated isopropanol of the following formula (IV):

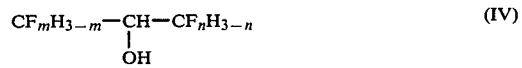
$$CF_mH_{3-m}-\underset{\underset{OH}{|}}{CH}-CF_nH_{3-n} \quad (IV)$$

wherein m and n are each an interger satisfying the formula: $4 \leq m+n \leq 6$, and further (E) a catalyst co-activator of at least one compound selected from halogenated compounds of the following formula (V) and (VI):

(V)

and

$$R^4R^5R^6CX \quad (VI)$$

wherein X is a halogen atom, $R^4$, $R^5$ and $R^6$ are each an alkyl, and n is an integer of 1 to 3, in an amount of 0 mole to less than equimolar to the trialkylaluminum, and optionally, to improve more the uniformity of the catalyst system, (F) a compound selected from an aliphatic alcohol having 10 to 20 carbon atoms and an aliphatic carboxylic acid having 10 to 20 carbon atoms or an ester thereof in an amount of 0.05 to 0.8 mole per 1 mole of the component (B).

In this specification, the term "alkyl" denotes a straight or branched alkyl having 1 to 18 carbon atoms, preferably 1 to 12 carbon atoms, such as methyl, ethyl, propyl, isopropyl, butyl, tert-butyl, amyl, isoamyl, hexyl, heptyl, octyl, nonyl, decyl, undecyl, and dodecyl; and the term "cycloalkyl" denotes a cycloalkyl having 3 to 7 carbon atoms, such as cyclopropyl, cyclobutyl, cyclopentyl, cyclohexyl and cycloheptyl. The term "aryl" denotes a phenyl which may be substituted with one to three alkyl or alkoxy groups having 1 to 3 carbon atoms, such as phenyl, o-, m- or p-tolyl, xylyl, 2,4,6-trimethylphenyl, p-isopropylphenyl, p-methoxyphenyl, o-, m- or p-ethylphenyl, and p-ethoxyphenyl; the term "aralkyl" denotes a phenylalkyl having 1 to 3 carbon atoms in the alkyl moiety, such as benzyl, phenethyl; and the "halogen" denotes fluorine, bromine, chlorine and iodine.

The organic acid salt of nickel (A) used as the catalyst component in this invention includes, for example, carboxylic acid salts of nickel, such as nickel naphthenate, nickel octate, nickel stearate, nickel formate, nickel acetate, nickel benzoate, nickel oxalate, etc. The complex of nickel includes bis-acetyl acetonato nickel, bis-dimethylglyoximate nickel, etc. which are easily prepared and stable. The complex of nickel may also include nickel complex compounds with an organic phosphine used as the component (C), for example, bis-tricyclohexylphosphine nickel chloride, bis-triisopropylphosphine nickel chloride, bis-triphenylphosphine nickel chloride, bis-trisdimethylaminophosphine nickel chloride, bis-tris(diisopropylamino)phosphine nickel chloride, etc. and also the corresponding bromide compounds of these chloride compounds.

The trialkylaluminum (B) includes trimethylaluminum, triethylaluminum, tri-n-propylaluminum, tri-isopropylaluminum, tri-n-butylaluminum, tri-isobutylaluminum, tri-n-pentylaluminum, tri-n-hexylaluminum, tricyclohexylaluminum, and the like.

Among the trivalent phosphorus compounds (C), the organic phosphine compound of the formula $PR^1R^2R^3$ includes trimethylphosphine, triethylphosphine, tri-n-propyl phosphine, tri-isopropylphosphine, tri-n-butylphosphine, tri-isobutylphosphine, tri-tert-butylphosphine, tri-sec-butylphosphine, tricyclopropylphosphine, tricyclohexylphosphine, triphenylphosphine, tri-p-tolylphosphine, tri-p-methoxyphenylphosphine, tri-2,4,6-trimethylphenylphosphine, phenyl-di-isopropylphosphine, ethyl-di-isopropylphosphine, ethyl-di-tert-butylphosphine, ethyl-di-cyclohexylphosphine, methyl-propyl-phenylphosphine, methyl-phenyl-benzylphosphine, and the like.

The aminophosphine compound of the formula: $P(NR^1_2)_3$ (II) includes tris-dimethylaminophosphine, tris-diethylaminophosphine, tris-di-n-propylaminophosphine, tris-di-isopropylaminophosphine, tris-di-n-butylaminophosphine, tris-di-isobutylaminophosphine, tris-di-tert-butylaminophosphine, tris-di-cyclohexylaminophosphine, and the like.

The phosphite compound of the formula: $P(OR^1)_3$ (III) includes trimethylphosphite, triethylphosphite, tri-n-propylphosphite, tri-isopropylphosphite, tri-n-butylphosphite, tri-isobutylphosphite, tri-tert-butylphosphite, tricyclohexylphosphite, triphenylphosphite, tri-p-tolylphosphite, tri-p-methoxyphenylphosphite, and the like.

These trivalent phosphorus compounds are the most effective on the distribution of isomers of the dimers. For instance, to obtain 2,3-dimethylbutenes in high selectivity by the dimerization of propylene, it is preferable to use organic phosphines such as tri-isopropylphosphine, tricyclohexylphosphine, tri-sec-butylphosphine, etc.

The fluorinated isopropanols of the formula (IV) used as the catalyst component (D) include 1,1,3,3-tetrafluoroisopropanol, 1,1,1,3-tetrafluoroisopropanol, 1,1,1,3,3-pentafluoroisopropanol, 1,1,1,3,3,3-hexafluoroisopropanol, and the like. Among these, 1,1,1,3,3,3-hexafluoropropanol is particularly preferable.

The fluorinated alcohol is essential for exhibiting the catalytic activity in the dimerization, and in the absence of the fluorinated alcohol, the catalyst of this invention substantially cannot exhibit the activity for dimerization of α-olefins. By varying the amount of the fluorinated alcohol, there can be controlled the distribution of the isomers having a double bond in the olefin dimers. For instance, in the case of producing selectivity 2,3-dimethylbutenes by the dimerization of propylene, when the fluorinated alcohol is used in a smaller amount, there is obtained 2,3-dimethylbutene-1, but when the amount is increased, there is obtained 2,3-dimethylbutene-2.

The compound of the formula (V) used as the catalyst co-activator in this invention includes benzotrichloride, benzal chloride, benzyl chloride, benzotribromide, benzal bromide, benzyl bromide, and the like. The compound of the formula (VI) includes tert-butyl chloride, tert-amyl chloride, tert-heptyl chloride, tert-butyl bromide, tert-amyl bromide, tert-heptyl bromide, and the like. The catalyst system used in this invention can exhibit the desired catalytic activity for the dimerization of olefines without such a catalyst co-activator as mentioned above, but the catalyst co-activator is occasionally effective. The catalyst co-activator is used in an amount of less than an equimolar amount to the trialkylaluminum (B), preferably less than 0.5 mole per 1 mole of the trialkylaluminum (B). When the catalyst co-activator is used in an amount more than equimolar amount to the trialkylaluminum, in the case of the production of 2,3-dimethylbutenes by dimerization of propylene, the selectivity of DMBS fraction in the dimers lowers, and hence, one of the characteristic effects of this invention is not achieved.

When an aliphatic alcohol, an aliphatic carboxylic acid, or an ester thereof is additionally incorporated into the catalyst system comprising the above four components (A), (B), (C) and (D) or five components (A), (B), (C), (D) and (E), the uniformity of the catalyst system is improved more. The aliphatic alcohol includes saturated or unsaturated aliphatic alcohols having 10 to 20 carbon atoms, such as n-decyl alcohol, n-undecyl alcohol, lauryl alcohol, myristyl alcohol, cetyl alcohol, stearyl alcohol, n-eicosyl alcohol, linderyl alcohol, 7-hexadecenol, oleyl alcohol, and the like.

The aliphatic carboxylic acid includes saturated or unsaturated aliphatic carboxylic acids having 10 to 20 carbon atoms, such as capric acid, lauric acid, myristic acid, palmitic acid, stearic acid, arachic acid, linderic acid, palmito-oleic acid, oleic acid, gadoleic acid, and the like.

The ester of the aliphatic carboxylic acid includes esters of the above aliphatic carboxylic acids with an alkyl having 1 to 6 carbon atoms, such as methyl, ethyl, n-propyl, isopropyl, n-butyl, tert-butyl, n-pentyl, isoamyl, n-hexyl, etc.

These aliphatic alcohols, carboxylic acids and esters thereof are effective for preventing the precipitation of catalyst components and hence for making the catalyst system uniform. These agents are used in an amount of 0.05 to 0.8 mole, preferably 0.1 to 0.5 mole, per 1 mole of the trialkylaluminum (B). When these agents are used in an amount larger than the above range, the catalyst loses its activity, while they show a larger prevention effect of precipitation of the catalyst components, and hence, it is preferable to use in an amount within the above range.

The catalyst system in the present invention can be prepared in the presence of the starting lower α-olefin, or preferably in the presence of a chain conjugated diolefin which functions as a catalyst stabilizer. The catalyst stabilizer includes conjugated diolefins such as butadiene, isoprene, 1,3-pentadiene, and the like. They are used in an amount of not more than 200 moles per 1 mole of the nickel compound (A). Even when they are used in an amount larger than the above range, the stabilizing effect is not increased to a higher degree.

In the preparation of the catalyst system, the order of addition of the components is not specified but any order may be applicable. In a preferred embodiment, in the presence of a small amount of the α-olefin or a stabilizer (i.e. a conjugated diolefin), the nickel compound (A), the trivalent phosphorus compound (C), the trialkylaluminum (B) and the fluorinated isopropanol are added in this order, alternatively, in the order of the components (A), (C), (D) and (B), or (C), (A), (B) and (D). The order of addition of the catalyst activators of the formulae (V) and (VI) is not specified, either. Besides, the agent (F) for the prevention of the precipitation of catalyst components can also be added in any order.

The catalyst components are usually incorporated in the following molar ratios: (B)/(A)=2 to 500, preferably 5 to 100; (C)/(A)=0.1 to 50, preferably 0.5 to 20; (D)/(B)=0.2 to 10, preferably 0.5 to 5; (E)/(B)=0 to 0.9, preferably not more than 0.5; and (F)/(B)=0 to 0.9, preferably not more than 0.5.

The catalyst system of this invention is usually prepared by mixing the components in any order in the presence of an α-olefin or stabilizer as mentioned above in an appropriate inert solvent. The solvent includes aromatic hydrocarbons (e.g. benzene, toluene, xylent, etc.), aliphatic hydrocarbons (e.g. hexane, heptane, cyclohexane, etc.), halogenated aromatic hydrocarbons (e.g. chlorobenzene, dichlorobenzene, etc.), and the like among which the aromatic hydrocarbons and halogenated aromatic hydrocarbons are preferable. The mixing of the catalyst components is usually carried out at a temperature of −80° to 60° C., preferably −20° to 40° C.

The dimerization reaction of lower α-olefins by this invention is usually carried out in the same inert solvents as mentioned above, but may optionally be carried out in a liquified lower α-olefin. In the dimerization reaction, the catalyst system is used in a concentration of $10^{-5}$ to $10^{-1}$ mole/liter which is calculated as the nickel component in the reaction system. The dimerization reaction is carried out at a temperature of −80° to 60° C., preferably −20° to 40° C., under atmospheric pressure or under equilibrium pressure which naturally occurs depending on the reaction temperature.

The dimerization of this invention is applicable to various lower α-olefins, such as ethylene, propylene, 1-butene, and the like.

After the dimerization reaction, the reaction is terminated by a conventional method, and after removal of the catalyst, the reaction product is isolated by rectification. The product can be analyzed and quantitatively measured by gas chromatography.

According to this invention, there can be eliminated various problems such as corrosion of the apparatus, non-uniformity of the catalyst system in the reaction system which are observed in the known processes. Further, the catalytic efficiency and selectivity of isomers of the dimers is improved more. Moreover, by varying the amount of the fluorinated isopropanol, the distribution of the double bond isomers in the dimers can also be controlled.

The present invention is illustrated by the following Examples, but should not be construed to be limited thereto.

EXAMPLE 1

A 100 ml stainless steel autoclave is deaerated, followed by replacement with nitrogen. To the autoclave are added a solution of nickel naphthenate (0.045 mmol) in toluene (0.45 ml), a solution of tricyclohexylphosphine (0.045 mmole) in toluene (0.45 ml), and isoprene (3.6 mmole, 0.36 ml) in this order, and thereto is added a solution of triethylaluminum (0.45 mmole) in toluene (0.42 ml) under ice-cooling, and the mixture is stirred. To the mixture is added a solution of 1,1,1,3,3,3-hexafluoroisopropanol (hereinafter referred to as "HFIP", 1.35 mmole) in toluene (1.35 ml) under ice-cooling with stirring, and the mixture is further stirred for 15 minutes. To the resulting catalyst solution is added dry toluene, and then charged propylene under a constant pressure of 4 kg/cm² and the mixture is reacted with stirring at 20° C. for 30 minutes.

After the reaction, the reaction mixture is analyzed by gas chromatography (n-pentane being used as an internal standard) by sampling of the mixture under pressure. The results are shown in Table 1. The reaction mixture obtained after purging the unreacted propylene is clear and there is observed no deposition on the wall of the autoclave.

EXAMPLE 2

In the same manner as described in Example 1 except that the amount of HFIP is changed to 0.675 mmole, the reaction is carried out. The results are shown in Table 1.

TABLE 1

| Ex. No. | Catalytic efficiency[1] | Selectivity[2] of dimers (%) | Selectivity[3] of DMBS (%) | Distribution of dimers (%) | | | | | | Ratio[4] of isomerization (%) |
| --- | --- | --- | --- | --- | --- | --- | --- | --- | --- | --- |
| | | | | 2,3-dimethyl-1-butene | 2,3-dimethyl-2-butene | 4-methyl-2-pentene | 2-methyl-1-pentene | 2-methyl-2-pentene | 2-hexene | |
| 1 | 23.4 × 10³ | 41.1 | 89.4 | 5.8 | 83.6 | 2.0 | 0.3 | 6.8 | 1.5 | 93.5 |

TABLE 1-continued

| Ex. No. | Catalytic efficiency[1] | Selectivity of dimers (%)[2] | Selectivity of DMBS (%)[3] | 2,3-dimethyl-1-butene | 2,3-dimethyl-2-butene | 4-methyl-2-pentene | 2-methyl-1-pentene | 2-methyl-2-pentene | 2-hexene | Ratio[4] of isomerization (%) |
|---|---|---|---|---|---|---|---|---|---|---|
| 2 | $17.1 \times 10^3$ | 53.4 | 86.0 | 85.3 | 0.7 | 3.0 | 7.5 | 2.0 | 1.5 | 0.8 |

[Notes]:
[1] Catalytic efficiency to the converted propylene ($C_3'$) (mole · propylene/g atom of Ni · hr)
[2] Fraction of dimers in the converted propylene
[3] Fraction of 2,3-dimethylbutenes in the dimers
[4] (2,3-dimethyl-2-butene/2,3-dimethylbutenes) × 100

EXAMPLE 3

A 100 ml stainless steel autoclave is deaerated, followed by replacement with nitrogen. To the autoclave are added a solution of nickel naphthenate (0.045 mmole) in toluene (0.45 ml), a solution of tricyclohexylphosphine (0.045 mmole) in toluene (0.45 ml), and isoprene (1.8 mmole, 0.18 ml) in this order, and thereto is added a solution of triethylaluminum (0.45 mmole) in toluene (0.42 ml) under ice-cooling, and the mixture is stirred. To the mixture is added a solution of tert-butyl chloride (0.045 mmole) in toluene (0.45 ml) under ice-cooling with stirring and the mixture is stirred for 5 minutes, and there is further added a solution of HFIP (1.35 mmole) in toluene (1.35 ml), and the mixture is further stirred for 15 minutes. To the resulting catalyst solution is added dry toluene, and then charged propylene under a constant pressure of 4 kg/cm² and the mixture is reacted with stirring at 20° C. for 30 minutes.

After the reaction, the reaction mixture is analyzed in the same manner as described in Example 1. The results are shown in Table 2. The reaction mixture is clear and there is observed no deposition on the wall of the autoclave.

EXAMPLES 4 TO 6

In the same manner as described in Example 3 except that the amount of tert-butyl chloride is changed as shown in Table 2, the reaction is carried out. The results are shown in Table 2.

TABLE 2

| Ex. No. | Amount of tert-butyl chloride (mmole) | Catalytic efficiency | Selectivity of dimers (%) | Selectivity of DMBS (%) | 2,3-dimethyl-1-butene | 2,3-dimethyl-2-butene | 4-methyl-2-pentene | 2-methyl-1-pentene | 2-methyl-2-pentene | 2-hexene | Ratio of isomerization (%) |
|---|---|---|---|---|---|---|---|---|---|---|---|
| 3 | 0.045 | $30.3 \times 10^3$ | 66.6 | 82.8 | 4.8 | 78.0 | 4.4 | 1.5 | 11.3 | 0 | 94.2 |
| 4 | 0.090 | $27.9 \times 10^3$ | 72.5 | 78.8 | 4.4 | 74.4 | 7.2 | 1.5 | 12.5 | 0 | 94.4 |
| 5 | 0.135 | $31.0 \times 10^3$ | 78.9 | 74.7 | 6.1 | 68.6 | 8.8 | 1.6 | 14.9 | 0 | 91.9 |
| 6 | 0.225 | $37.5 \times 10^3$ | 87.8 | 71.4 | 4.4 | 67.0 | 12.0 | 1.8 | 14.8 | 0 | 93.9 |

EXAMPLES 7 TO 10

In the same manner as described in Example 3 except that the amount of tert-butyl chloride is 0.09 mmole and the amount of HFIP is changed as shown in Table 3, the reaction is carried out. The results are shown in Table 3.

TABLE 3

| Ex. No. | Amount of HFIP (mmole) | Catalytic efficiency | Selectivity of dimers (%) | Selectivity of DMBS (%) | 2,3-dimethyl-1-butene | 2,3-dimethyl-2-butene | 4-methyl-2-pentene | 2-methyl-1-pentene | 2-methyl-2-pentene | 2-hexene | Ratio of isomerization (%) |
|---|---|---|---|---|---|---|---|---|---|---|---|
| 7 | 0.9 | $22.3 \times 10^3$ | 79.9 | 74.0 | 63.9 | 10.1 | 11.3 | 8.0 | 5.9 | 0.8 | 13.7 |
| 8 | 1.35 | $27.9 \times 10^3$ | 72.5 | 78.8 | 4.4 | 74.4 | 7.2 | 1.5 | 12.5 | 0 | 94.4 |
| 9 | 1.8 | $33.3 \times 10^3$ | 71.0 | 79.4 | 5.6 | 73.8 | 5.8 | 1.5 | 13.3 | 0 | 93.0 |
| 10 | 2.25 | $30.9 \times 10^3$ | 64.5 | 82.6 | 5.3 | 77.3 | 4.6 | 1.4 | 11.4 | 0 | 93.6 |

EXAMPLES 11 TO 12

A 100 ml stainless steel autoclave is deaerated, followed by replacement with nitrogen. To the autoclave are added a solution of bis-triisopropylphosphine-nickel chloride (0.01 mmole) in toluene (0.5 ml) and isoprene (0.8 mmole, 0.08 ml), and thereto is added a solution of triethylaluminum (0.2 mmole) in toluene (0.5 ml) under ice-cooling, and the mixture is stirred for 5 minutes. To the mixture is added a solution of HFIP in an amount as shown in Table 4 under ice-cooling with stirring, and the mixture is further stirred for 15 minutes. To the resulting catalyst solution is added dry toluene (8.5 ml), and then charged propylene under a constant pressure of 4 kg/cm² and the mixture is reacted with stirring at 20° C. for 30 minutes.

After the reaction, the reaction mixture is analyzed in the same manner as described in Example 1. The results are shown in Table 4.

TABLE 4

| Ex. No. | Amount of HFIP (mmole) | Catalytic efficiency | Selectivity of dimers (%) | Selectivity of DMBS (%) | 2,3-dimethyl-1-butene | 2,3-dimethyl-2-butene | 4-methyl-2-pentene | 2-methyl-1-pentene | 2-methyl-2-pentene | 2-hexene | Ratio of isomerization (%) |
|---|---|---|---|---|---|---|---|---|---|---|---|
| 11 | 0.3 | $88.8 \times 10^3$ | 93.1 | 61.0 | 60.6 | 0.4 | 18.5 | 11.5 | 7.2 | 1.2 | 0.6 |

TABLE 4-continued

| Ex. No. | Amount of HFIP (mmole) | Catalytic efficiency | Selectivity of dimers (%) | Selectivity of DMBS (%) | Distribution of dimers (%) | | | | | | Ratio of isomerization (%) |
|---|---|---|---|---|---|---|---|---|---|---|---|
| | | | | | 2,3-di-methyl-1-butene | 2,3-di-methyl-2-butene | 4-methyl-2-pentene | 2-methyl-1-pentene | 2-methyl-2-pentene | 2-hexene | |
| 12 | 0.5 | 80.2 × 10³ | 71.4 | 77.9 | 6.2 | 71.7 | 9.0 | 1.5 | 11.6 | 0 | 92.0 |

EXAMPLES 13

In the same manner as described in Example 4 except that benzyl chloride (0.09 mmole) is used instead of tert-butyl chloride (0.09 mmole), the reaction is carried out. The results are shown in Table 5.

TABLE 5

| Ex. No. | Catalytic efficiency | Selectivity of dimers (%) | Selectivity of DMBS (%) | Distribution of dimers (%) | | | | | | Ratio of isomerization (%) |
|---|---|---|---|---|---|---|---|---|---|---|
| | | | | 2,3-di-methyl-1-butene | 2,3-di-methyl-2-butene | 4-methyl-2-pentene | 2-methyl-1-pentene | 2-methyl-2-pentene | 2-hexene | |
| 13 | 30.0 × 10³ | 73.5 | 79.3 | 4.8 | 74.5 | 6.0 | 1.9 | 12.8 | 0 | 94.0 |

EXAMPLES 14 TO 19

In the same manner as described in Example 3 except that various organic phosphorus compounds as shown in Table 6 are used instead of tricyclohexylphosphine, the reaction is carried out. The results are shown in Table 6.

A 100 ml stainless steel autoclave is deaerated, followed by replacement with nitrogen. To the autoclave are added a solution of nickel naphthenate (0.1 mmole) in chlorobenzene (1 ml), a solution of tricyclohexylphosphine (0.1 mmole) in chlorobenzene (1 ml), and isoprene (8 mmole, 0.8 ml) in this order, and thereto is added a solution of triethylaluminum (1.0 mmole) in chlorobenzene (1 ml) under ice-cooling, and the mixture is stirred. To the mixture is added a solution of HFIP (3 mmole) in chlorobenzene (3 ml) under ice-cooling with stirring, and the mixture is further stirred for 15 minutes. To the resulting catalyst solution is added dry chlorobenzene (3.7 ml), and then charged

TABLE 6

| Ex. No. | Organic phosphorus compound | Catalytic efficiency | Selectivity of dimers (%) | Distribution of dimers (%) | | | | | |
|---|---|---|---|---|---|---|---|---|---|
| | | | | 2,3-di-methyl-1-butene | 2,3-di-methyl-2-butene | 4-methyl-2-pentene | 2-methyl-1-pentene | 2-methyl-2-pentene | 2-hexene |
| 14 | P(i-Pr)₃ | 25.4 × 10³ | 68.5 | 4.0 | 77.0 | 4.7 | 1.6 | 12.7 | 0 |
| 15 | P(sec-Bu)₃ | 32.3 × 10³ | 67.0 | 5.1 | 79.2 | 4.3 | 1.5 | 9.9 | 0 |
| 16 | P(n-Bu)₃ | 51.0 × 10³ | 86.7 | 2.8 | 42.0 | 10.7 | 4.2 | 40.3 | 0 |
| 17 | P(C₆H₁₁)₃ 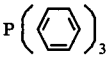 | 8.6 × 10³ | 66.6 | 1.6 | 20.7 | 15.9 | 5.7 | 53.0 | 3.1 |
| 18 | P(O-C₆H₅)₃ 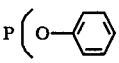 | 7.0 × 10³ | 68.6 | 0.8 | 11.6 | 10.8 | 7.7 | 69.0 | 0 |
| 19 | P(NMe₂)₃ | 4.2 × 10³ | 60.4 | 2.1 | 28.5 | 24.3 | 5.1 | 38.3 | 1.7 |

EXAMPLE 20

In the same manner as described in Example 3 except that 1,1,1,3-tetrafluoroisopropanol (1.35 mmole) is used instead of HFIP, the reaction is carried out. The results are shown in Table 7.

propylene under a constant pressure of 4 kg/cm², and the mixture is reacted with stirring at 20° C. for one hour.

After the reaction, the reaction mixture is analyzed in the same manner as described in Example 1. The results are shown in Table 8. The reaction mixture thus ob-

TABLE 7

| Ex. No. | Catalytic efficiency | Selectivity of dimers (%) | Selectivity of DMBS (%) | Distribution of dimers (%) | | | | | | Ratio of isomerization (%) |
|---|---|---|---|---|---|---|---|---|---|---|
| | | | | 2,3-di-methyl-1-butene | 2,3-di-methyl-2-butene | 4-methyl-2-pentene | 2-methyl-1-pentene | 2-methyl-2-pentene | 2-hexene | |
| 20 | 15.6 × 10³ | 79.4 | 75.0 | 66.0 | 9.0 | 11.0 | 7.8 | 6.2 | 0 | 12.0 |

EXAMPLE 21

To confirm the uniformity of the catalyst system, the following promotion test is carried out by increasing the concentration of the catalyst components.

tained is clear and there are observed a few depositions on the bottom of the reactor.

TABLE 8

| Ex. No. | Catalytic efficiency | Selectivity of dimers (%) | Selectivity of DMBS (%) | Distribution of dimers (%) | | | | | | Ratio of isomerization (%) |
|---|---|---|---|---|---|---|---|---|---|---|
| | | | | 2,3-di-methyl-1-butene | 2,3-di-methyl-2-butene | 4-methyl-2-pentene | 2-methyl-1-pentene | 2-methyl-2-pentene | 2-hexene | |
| 21 | 9.5 × 10³ | 61.0 | 89.0 | 4.9 | 84.1 | 1.5 | 1.3 | 8.2 | 0 | 94.5 |

REFERENCE EXAMPLE 1

In the same manner as described in Example 3 except that 1,1,1-trifluoroisopropanol (1.35 mmole) is used instead of HFIP, the reaction is carried out. The results are shown in Table 9.

REFERENCE EXAMPLE 2

In the same manner as described in Example 21 wherein trichlorophenol is used instead of HFIP, a test is carried out as follows.

A 100 ml stainless steel autoclave is deaerated, followed by replacement with nitrogen. To the autoclave are added a solution of nickel naphthenate (0.1 mmole) in chlorobenzene (1 ml), a solution of tricyclohexylphosphine (0.1 mmole) in chlorobenzene (1 ml), isoprene (8 mmole, 0.8 ml) and water (0.5 mmole, 9 μl) in this order, and thereto is added a solution of triethylaluminum (1.0 mmole) in chlorobenzene (1 ml) under ice-cooling, and the mixture is stirred. To the mixture is added a solution of 2,4,6-trichlorophenol (3 mmole) in chlorobenzene (3 ml) under ice-cooling with stirring, and the mixture is further stirred for 15 minutes. To the resulting catalyst solution is added dry chlorobenzene (3.7 ml), and then charged propylene under a constant pressure of 4 kg/cm² and the mixture is reacted with stirring at 20° C. for one hour.

After the reaction, the reaction mixture is analyzed in the same manner as described in Example 1. The results are shown in Table 9. The reaction mixture thus is unclear and there are observed depositions on the bottom of the reactor.

A 100 ml Schlenk's tube is deaerated, followed by replacement with nitrogen. To the tube are added a solution of nickel naphthenate (0.4 mmole) in toluene (2.0 ml), a solution of tricyclohexylphosphine (0.4 mmole) in toluene (1 ml), isoprene (32 mmole, 3.2 ml), and a solution of triethylaluminum (4 mmole) in toluene (4 ml) in this order, and the mixture is stirred for 5 minutes under ice-cooling. To the mixture are added a solution of tert-butyl chloride (0.8 mmole) in toluene (0.8 ml), a solution of each of various additives as shown in Table 10 (1.2 mmole) in toluene (12 ml), and a solution of HFIP (12 mmole) in toluene (8 ml) in this order under ice-cooling with stirring, and the mixture is further stirred for 15 minutes. To the resulting catalyst solution is added dry toluene so as to be 45 ml in volume.

Separately, a 1.5 liter stainless steel autoclave is deaerated, followed by replacement with nitrogen, to which is charged dry toluene (70 ml), and then the autoclave is sealed. To the reactor are charged the catalyst as prepared above (45 ml) and propylene (440 g), which are added in portions over a period of 4 hours at 20° C. with stirring, and thereafter, the reaction is continued for 3 hours at 20° C. with stirring.

After the reaction, the reaction mixture is analyzed by gas chromatography (n-pentane being used as an internal standard) by sampling of the mixture under pressure. The results are shown in Table 10.

After purging the unreacted propylene from the autoclave, it is opened, and the reaction mixture is drained. The state of deposition on the wall or bottom of the reactor is observed. The results are shown in Table 10.

TABLE 9

| Ex. No. | Catalytic efficiency | Selectivity of dimers (%) | Selectivity of DMBS (%) | Distribution of dimers (%) | | | | | | Ratio of isomerization (%) |
|---|---|---|---|---|---|---|---|---|---|---|
| | | | | 2,3-di-methyl-1-butene | 2,3-di-methyl-2-butene | 4-methyl-2-pentene | 2-methyl-1-pentene | 2-methyl-1-pentene | 2-hexene | |
| Ref. Ex. 1 | 4.0 × 10³ | 85.0 | 64.8 | 64.8 | 0 | 17.5 | 9.4 | 8.3 | 0 | 0 |
| Ref. Ex. 2 | 7.8 × 10³ | 57.2 | 86.5 | 4.8 | 81.7 | 2.3 | 1.3 | 10.0 | 0 | 94.5 |

TABLE 10

| No. | Additives | Conversion of propylene (%) | Selectivity of dimers (%) | Selectivity of DMBS (%) | Isomeri-*¹ zation ratio (%) | State of deposition on wall and bottom of the reactor*² |
|---|---|---|---|---|---|---|
| 1 | Stearic acid | 98.7 | 66.3 | 82.2 | 94.9 | — |
| 2 | Ethyl stearate | 94.4 | 69.4 | 78.9 | 94.3 | — |
| 3 | Oleic acid | 96.4 | 70.1 | 79.2 | 94.8 | — |
| 4 | Ethyl oleate | 96.3 | 67.4 | 78.9 | 94.3 | — |
| 5 | Stearyl alcohol | 94.5 | 50.8 | 84.0 | 94.5 | — |
| 6 | — | 98.5 | 68.9 | 82.9 | 95.2 | ± |

*¹(2,3-dimethyl-2-butene/2,3-dimethylbutenes) × 100
*²+: significant depositions, ±: a few depositions, —: no deposition

EXAMPLE 22

In order to study the state of the deposition of catalyst in more detail, the reaction is carried out in a scale up system as follows.

EXAMPLE 23

In the same manner as described in Example 22 except that the amount of stearic acid is changed from 1.2 mmole to the amount as shown in Table 11, the reaction is carried out. The results are shown in Table 11.

TABLE 11

| Run No. | Amount of stearic acid | Conversion of propylene (%) | Selectivity of dimers (%) | Selectivity of DMBS (%) | Isomerization ratio (%) | State of deposition on wall and bottom of the reactor |
|---|---|---|---|---|---|---|
| 1 | 0.4 | 97.8 | 69.5 | 81.3 | 94.5 | — |
| 2 | 0.8 | 98.8 | 66.4 | 82.7 | 95.1 | — |
| 3 | 1.4 | 97.1 | 67.1 | 81.2 | 94.9 | — |

EXAMPLE 24

In the same manner as described in Example 1 except that various additives as shown in Table 12 (each 1.6 mmole) are used, the reaction is carried out. The results are shown in Table 12.

TABLE 12

| Run No. | Additives | Conversion of propylene (%) | Selectivity of dimers (%) | Selectivity of DMBS (%) | Isomerization ratio (%) | State of deposition on wall and bottom of the reactor |
|---|---|---|---|---|---|---|
| 1 | Lauryl alcohol | 84.5 | 64.0 | 82.4 | 90.3 | — |
| 2 | n-Dodecyl alcohol | 90.0 | 64.2 | 82.7 | 92.0 | — |
| 3 | n-Tetradecyl alcohol | 90.6 | 64.8 | 82.0 | 92.5 | — |
| 4 | Cetyl alcohol | 92.3 | 62.6 | 83.0 | 94.2 | — |
| 5 | n-Hepatadecyl alcohol | 92.0 | 64.0 | 82.5 | 94.0 | — |
| 6 | Stearyl alcohol | 92.4 | 62.3 | 84.5 | 94.2 | — |

EXAMPLE 25

In the same manner as described in Example 22 except that various carboxylic acids and esters as shown in Table 13 (each 1.2 mmole) are used, the reaction is carried out. The results are shown in Table 13.

TABLE 13

| Run No. | Additives | Conversion of propylene (%) | Selectivity of dimers (%) | Selectivity of DMBS (%) | Isomerization ratio (%) | State of deposition on wall and bottom of the reactor |
|---|---|---|---|---|---|---|
| 1 | Capric acid | 96.0 | 68.1 | 81.9 | 94.8 | — |
| 2 | Lauric acid | 97.8 | 64.9 | 82.3 | 94.9 | — |
| 3 | Myristic acid | 98.7 | 69.4 | 81.1 | 95.1 | — |
| 4 | Palmitic acid | 98.5 | 67.3 | 80.8 | 94.9 | — |
| 5 | Stearic acid | 98.7 | 66.3 | 82.2 | 94.9 | — |
| 6 | Oleic acid | 96.4 | 70.1 | 79.2 | 94.8 | — |
| 7 | Methyl stearate | 96.9 | 74.2 | 75.6 | 94.8 | — |
| 8 | Ethyl stearate | 94.4 | 69.4 | 78.9 | 94.3 | — |
| 9 | n-Butyl stearate | 98.4 | 67.7 | 80.6 | 95.0 | — |

What is claimed is:

1. A process for dimerizing lower α-olefins, which comprises dimerizing a lower α-olefin in the presence of a catalyst system comprising the following components:
    (A) an organic acid salt or complex of nickel,
    (B) a trialkylaluminum,
    (C) at least one trivalent phosphorus compound of the following formula (I), (II) or (III):

$$PR^1R^2R^3 \quad (I)$$

$$P(NR^1{}_2)_3 \quad (II)$$

$$P(OR^1)_3 \quad (III)$$

wherein $R^1$, $R^2$ and $R^3$ are independently an alkyl, a cycloalkyl, an aryl, or an aralkyl, and
    (D) a fluorinated isopropanol of the following formula (IV):

$$CF_mH_{3-m}-\underset{\underset{OH}{|}}{CH}-CF_nH_{3-n} \quad (IV)$$

wherein m and n are each an interger satisfying the formula: $4 \leq m+n \leq 6$, and
    (E) a catalyst co-activator of at least one compound selected from halogenated compounds of the following formulae (V) and (VI):

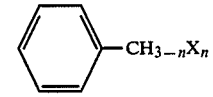
$$(V)$$

and $$R^4R^5R^6CX \quad (VI)$$

wherein X is a halogen atom, $R^4$, and $R^5$ and $R^6$ are each an alkyl, and n is an integer of 1 to 3, in an amount of 0 mole to less than equimolar to the trialkylaluminum.

2. The process according to claim 1, wherein there is incorporated as an agent for the prevention of the precipitation of catalyst components
    (F) a compound selected from an aliphatic alcohol having 10 to 20 carbon atoms and an aliphatic carboxylic acid having 10 to 20 carbon atoms or an ester thereof in an amount of 0.05 to 0.8 mole per 1 mole of the component (B).

3. The process according to claim 1, wherein the catalyst components are incorporated in the following molar ratios:

(B)/(A): 2 to 500, (C)/(A): 0.1 to 50, (D)/(B): 0.2 to 10, and (E)/(B): 0 to 0.9.

4. The process according to claim 3, wherein the molar ratios of the catalyst components are in the following ranges:

(B)/(A): 5 to 100, (C)/(A): 0.5 to 20, (D)/(B): 0.5 to 5, and (E)/(B): 0 to 0.5.

5. The process according to claim 1, wherein the dimerization reaction is carried out in a concentration of the catalyst system of $10^{-5}$ to $10^{-1}$ mole/liter as calculated as the nickel component.

* * * * *